United States Patent
Arhancet et al.

(10) Patent No.: US 10,240,029 B2
(45) Date of Patent: Mar. 26, 2019

(54) PLASTIC MODIFIERS

(71) Applicant: Novus International Inc., St. Charles, MO (US)

(72) Inventors: Graciela B. Arhancet, St. Charles, MO (US); Xiaojun Wang, St. Charles, MO (US); Scott Long, St. Charles, MO (US); Matthew William Mahoney, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 272 days.

(21) Appl. No.: 15/148,378

(22) Filed: May 6, 2016

(65) Prior Publication Data

US 2016/0326349 A1    Nov. 10, 2016

Related U.S. Application Data

(60) Provisional application No. 62/158,112, filed on May 7, 2015.

(51) Int. Cl.
| | | |
|---|---|---|
| *C08K 5/372* | (2006.01) | |
| *C07C 319/20* | (2006.01) | |
| *C07C 323/52* | (2006.01) | |
| *C08G 63/688* | (2006.01) | |
| *C08G 63/91* | (2006.01) | |
| *C08K 5/41* | (2006.01) | |
| *C08L 67/04* | (2006.01) | |

(52) U.S. Cl.
CPC ............ *C08K 5/372* (2013.01); *C07C 319/20* (2013.01); *C07C 323/52* (2013.01); *C08G 63/6882* (2013.01); *C08G 63/912* (2013.01); *C08K 5/41* (2013.01); *C08L 67/04* (2013.01)

(58) Field of Classification Search
CPC ...... C08L 2666/14; C08L 67/00; C08L 67/02; C08G 63/60
See application file for complete search history.

(56) References Cited

U.S. PATENT DOCUMENTS

| | | | |
|---|---|---|---|
| 2,848,466 A | 8/1958 | Fletcher | |
| 4,130,532 A | 12/1978 | Lamb | |
| 4,133,794 A | 1/1979 | Lamb | |
| 4,797,426 A * | 1/1989 | Waki | C08J 9/0014 521/134 |
| 8,084,551 B2 | 12/2011 | Ara | |
| 8,158,731 B2 | 4/2012 | Stefanisin | |
| 2007/0208105 A1* | 9/2007 | Grossman | C08J 5/18 523/124 |
| 2012/0283364 A1 | 11/2012 | Sarazin | |
| 2013/0178540 A1* | 7/2013 | Grady | C11D 1/002 514/785 |
| 2013/0209391 A1* | 8/2013 | Arhancet | C08G 67/00 424/78.37 |
| 2013/0209392 A1* | 8/2013 | Arhancet | C08G 67/00 424/78.38 |
| 2014/0011930 A1 | 1/2014 | Buono | |

FOREIGN PATENT DOCUMENTS

| | | |
|---|---|---|
| JP | H06326557 | 11/1994 |
| WO | 2008/006076 A2 | 1/2008 |
| WO | 2011/085058 A1 | 7/2011 |
| WO | 2013/119955 A1 | 8/2013 |
| WO | 2013/119959 A1 | 8/2013 |
| WO | 2016/179489 A1 | 11/2016 |

OTHER PUBLICATIONS

Labrecque et al., Citrate esters as plasticizers for polylactic acid), Journal of Applied Polymer Science, 1997, 66(8): 1507-1513.

Ljunhberg et al., The effects of plasticizers on the dynamic mechanical and thermal properties of poly(lactic acid), Journal of Applied Polymer Science, 2002, 86(5): 1227-1234.

López-Rodriguez et al., Plasticization of Poly-L-lactide with L-lactide, D-lactide, and D,L-lactide monomers, Polymer Engineering & Science, 2013, 53(10): 2073-2080.

Kulinski et al., Plasticization of Poly(I-lactide) with Poly(propylene glycol), Biomacromolecules, 2007, 7(7): 2128-2135.

Murariu et al., Polylactide (PLA) designed with desired end-use properties: 1. PLA compositions with low molecular weight ester-like plasticizers and related performances, Polymers for Advanced Technologies, 2008, 19(6): 636-646.

International Search Report and Written Opinion dated Aug. 11, 2016 from related International application No. PCT/US16/31202, 9 pp.

* cited by examiner

*Primary Examiner* — Christopher M Rodd

(74) *Attorney, Agent, or Firm* — Polsinelli PC

(57) ABSTRACT

Hydrocarbyl terminated polyester compounds comprising sulfur-containing repeat units that are useful as plastic modifiers, polymer blend compositions comprising the hydrocarbyl terminated polyester compounds, methods for modifying the performance properties of polymers, and methods for preparing the hydrocarbyl terminated polyester compounds.

23 Claims, No Drawings

PLASTIC MODIFIERS

CROSS REFERENCE TO RELATED APPLICATIONS

This application claims the priority of U.S. provisional Application No. 62/158,112, filed May 7, 2015, which is hereby incorporated by reference in its entirety.

FIELD OF THE INVENTION

The present disclosure generally relates to hydrocarbyl terminated polyester compounds having sulfur-containing repeat units that are useful as plastic modifiers. In particular, the disclosure relates to the polyester compounds, polymer blends comprising polymers and the polyester compounds, and methods of using the polyester compounds to modify performance properties of polymers.

BACKGROUND OF THE INVENTION

Non-biodegradable polymers, such as polyvinyl chloride (PVC), are used in a wide variety of consumer products. The functional properties of many polymers can be improved by the addition of additives such as plasticizers. Phthalates are the most commonly used plasticizers, but their use is being phased out because of concerns about health and environmental risks. Thus, there is a need for new functional and environmentally friendly plasticizers that provide the same performance benefits as phthalates and/or improve the performance properties of polymers such as PVC. For biodegradable polymers made from polylactide (PLA), a plasticizer is appreciated in terms of improving PLA performances and reducing production cycle time without sacrificing biodegradability of the end consumer products.

SUMMARY OF THE INVENTION

Among the various aspects of the present disclosure is the provision of a polyester composition comprising compounds of Formula (I):

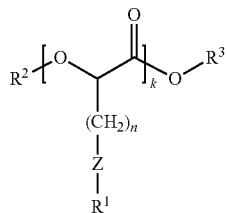

wherein:
$R^1$ and $R^3$ independently are hydrocarbyl or substituted hydrocarbyl;
$R^2$ is $R^4CO$— or $R^4$, wherein $R^4$ is hydrocarbyl or substituted hydrocarbyl;
Z is sulfur, sulfoxide, or sulfone;
k is an integer of 1 or greater; and
n is an integer of 1 or greater.

Another aspect of the present disclosure encompasses a polymer blend composition comprising a polymer and a polyester composition comprising compounds of Formula (I):

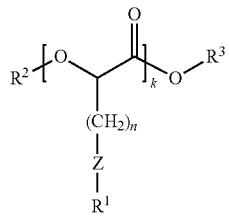

wherein:
$R^1$ and $R^3$ independently are hydrocarbyl or substituted hydrocarbyl;
$R^2$ is hydrogen, $R^4CO$—, or $R^4$, wherein $R^4$ is hydrocarbyl or substituted hydrocarbyl;
Z is sulfur, sulfoxide, or sulfone;
k is an integer of 1 or greater; and
n is an integer of 1 or greater.

A further aspect of the present disclosure provides a process for modifying performance properties of polymers. The process comprises contacting a polymer with a polyester composition comprising compounds of Formula (I) to form a polymer blend composition, wherein the polymer blend composition has an improved performance property relative to an unmodified polymer, the compounds of Formula (I):

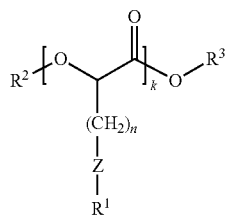

wherein:
$R^1$ and $R^3$ independently are hydrocarbyl or substituted hydrocarbyl;
$R^2$ is hydrogen, $R^4CO$—, or $R^4$, wherein $R^4$ is hydrocarbyl or substituted hydrocarbyl;
Z is sulfur, sulfoxide, or sulfone;
k is an integer of 1 or greater; and
n is an integer of 1 or greater.

Still another aspect of the present disclosure encompasses a process for preparing a polyester composition comprising compounds of Formula (Ia) from a compound of Formula (III). The process comprises (a) contacting the compound of Formula (III) with an alcohol, $R^3OH$, to form a distribution of compounds of Formula (II) and (b) contacting the distribution of compounds of Formula (II) with an acyl halide or its acid analog, $R^4C(O)X$, to form the polyester composition comprising compounds of Formula (Ia), according to the following reaction scheme:

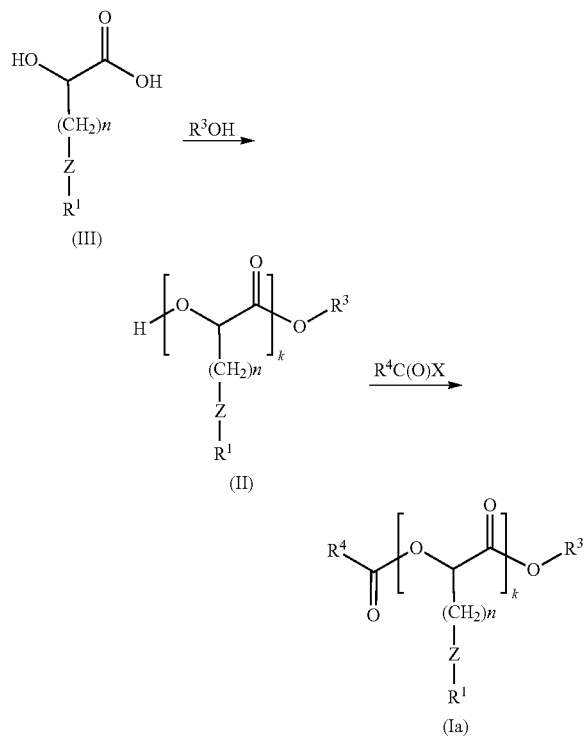

wherein:
R¹, R³, and R⁴ independently are hydrocarbyl or substituted hydrocarbyl;
X is a halide ion or a hydroxyl group;
Z is sulfur, sulfoxide, or sulfone;
k is an integer of 1 or greater; and
n is an integer of 1 or greater.

Yet another aspect of the present disclosure provides a process preparing a polyester composition comprising compounds of Formula (Ia) from a compound of Formula (IV). The process comprises (a) contacting the compound of Formula (IV) with an alcohol, R³OH, to form a distribution of compounds of Formula (II) and (b) contacting the distribution of compounds of Formula (II) with an acyl halide or its acid analog, R⁴C(O)X, to form the polyester composition comprising compounds of Formula (Ia), according to the following reaction scheme:

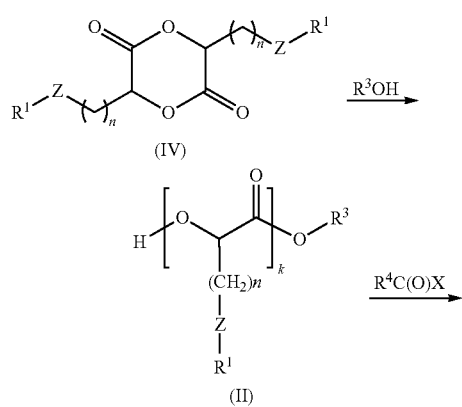

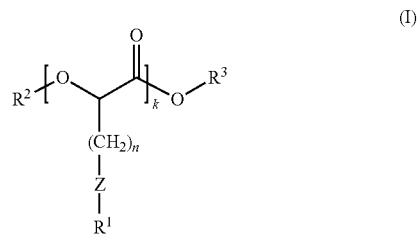

wherein:
R¹, R³, and R⁴ independently are hydrocarbyl or substituted hydrocarbyl;
X is a halide ion or a hydroxyl group;
Z is sulfur, sulfoxide, or sulfone;
k is an integer of 1 or greater; and
n is an integer of 1 or greater.

Other features and iterations of the invention are described in more detail below.

DETAILED DESCRIPTION OF THE INVENTION

The present disclosure provides hydrocarbyl terminated polyester compounds comprising sulfur-containing repeat units that are useful as plastic modifiers. In particular, the polyester compounds disclosed herein can be used to modify the performance properties of industrial plastics. For example, the polyester compounds can improve the flexibility and/or impact properties of polymers. Additionally, the polyester compounds disclosed herein have low migration and low toxicity. The present disclosure also provides polymer blends comprising polymers and the polyester compounds, as well as processes for preparing the polyester compounds.

(I) Polyester Compounds
  (a) Structure

One aspect of the present disclosure provides a polyester composition comprising compounds of Formula (I):

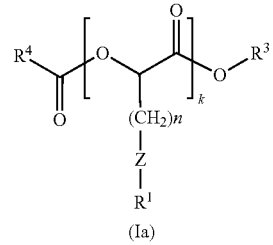

wherein:
R¹ and R³ independently are hydrocarbyl or substituted hydrocarbyl;
R² is hydrogen, R⁴CO—, or R⁴, wherein R⁴ is hydrocarbyl or substituted hydrocarbyl
Z is sulfur, sulfoxide, or sulfone;
k is an integer of 1 or greater; and
n is an integer of 1 or greater.

In various embodiments, R¹ may be alkyl, alkenyl, alkynyl, aryl, substituted alkyl, substituted alkenyl, substituted alkynyl, or substituted aryl. Additionally, R¹ in each repeat unit may differ. In some embodiments, R¹ may be $C_1$ to $C_6$ alkyl or $C_1$ to $C_6$ alkenyl, wherein alkyl and alkenyl may be linear, branched, or cyclic. In certain embodiments, R¹ may be methyl, ethyl, propyl, isopropyl, butyl, tert-butyl, hexyl, cyclohexyl, and the like. In specific embodiments, $R^1$ may be methyl.

In certain embodiments, $R^2$ may be $R^4CO-$, wherein $R^4$ may be alkyl, substituted alkyl, alkenyl, substituted alkenyl, aryl, or substituted aryl, and alkyl or alkenyl may be linear or branched. In some embodiments in which $R^2$ is $R^4CO-$, $R^4$ may be $C_1$ to $C_{30}$ alkyl or $C_1$ to $C_{30}$ alkenyl. In other embodiments in which $R^2$ is $R^4CO-$, $R^4$ may be $C_1$ to $C_{22}$ alkyl or $C_1$ to $C_{22}$ alkenyl. In further embodiments in which $R^2$ is $R^4CO-$, $R^4$ may be methyl, ethyl, propyl, butyl, pentyl, hexyl, heptyl, octyl, nonyl, decyl, dodecyl, tetradecyl, hexadecyl, octadecyl, eicosanyl, or docosanyl. In other embodiments, $R^2$ may be $R^4$, wherein $R^4$ may be alkyl, substituted alkyl, alkenyl, substituted alkenyl, aryl, or substituted aryl, wherein alkyl and alkenyl may be linear or branched. In some embodiments in which $R^2$ is $R^4$, $R^4$ may be $C_1$ to $C_{30}$ alkyl or $C_1$ to $C_{30}$ alkenyl. In other embodiments in which $R^2$ is $R^4$, $R^4$ may be $C_1$ to $C_{22}$ alkyl or $C_1$ to $C_{22}$ alkenyl. In further embodiments in which $R^2$ is $R^4$, $R^4$ may be methyl, ethyl, propyl, butyl, pentyl, hexyl, heptyl, octyl, nonyl, decyl, dodecyl, tetradecyl, hexadecyl, octadecyl, eicosanyl, or docosanyl. In still other embodiments, $R^2$ may be hydrogen.

In some embodiments, $R^3$ may be alkyl, substituted alkyl, alkenyl, substituted alkenyl, aryl, or substituted aryl, wherein alkyl and alkenyl may be linear or branched. In certain embodiments, $R^3$ may be $C_1$ to $C_{30}$ alkyl, or $C_1$ to $C_{30}$ alkenyl. In other embodiments, $R^3$ may be $C_1$ to $C_{22}$ alkyl or $C_1$ to $C_{22}$ alkenyl. In particular embodiments, $R^3$ may be methyl, ethyl, propyl, butyl, pentyl, hexyl, heptyl, octyl, nonyl, decyl, dodecyl, tetradecyl, hexadecyl, octadecyl, eicosanyl, or docosanyl.

In some embodiments, Z may be sulfoxide. In other embodiments, Z may be sulfone. In specific embodiments, Z may be sulfur.

In some embodiments, n may be an integer from 1 to 20, from 1 to 10, or from 1 to 6. In certain embodiments, n may be 1, 2, 3, or 4. In specific embodiments, n may be 2.

In general, k may range from 1 to several thousand. In some embodiments, k may range from 1 to about 500, from 1 to about 100, from 1 to about 50, or from 1 to about 20. In certain embodiments, k may range from 1 to 10, from 1 to 9, from 1 to 8, from 1 to 7, from 1 to 6, from 1 to 5, from 1 to 4, or from 1 to 3. While it is understood that polyesters embody a distribution of molecules, individual molecules also are included in this disclosure (i.e., k is 1, k is 2, k is 3, and the like).

In exemplary embodiments, $R^1$ is methyl; $R^2$ is $R^4CO-$ or $R^4$, wherein $R^4$ is alkyl, substituted alkyl, alkenyl, or substituted alkenyl; $R^3$ is alkyl, substituted alkyl, alkenyl, or substituted alkenyl; n is 2; k ranges from 1 to 20; and Z is sulfur.

(b) Stereochemistry

The polyester compounds having Formula (I) disclosed herein generally have at least one chiral center, as denoted with an asterisk in the schematic below

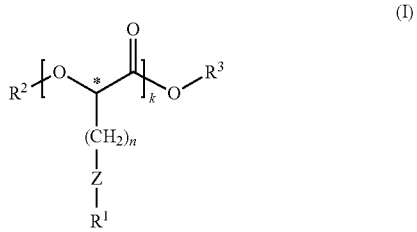

(I)

wherein $R^1$, $R^2$, $R^3$, Z, n, and k are as defined above. The compounds disclosed herein may comprise additional chiral centers.

Each chiral center may have an R or an S configuration. In compounds comprising one chiral carbon, the configuration may be R or S. In compounds comprising two or more chiral carbons, the configuration of each will be independently R or S. For example, in compounds comprising two chiral carbons, the configuration may be RR, RS, SR, or SS, in compounds comprising three chiral carbons, the configuration may be RRR, RRS, RSR, RSS, SRR, SRS, SSR, or SSS, and so forth.

(c) Properties

The polyester compounds disclosed herein represent a distribution of compounds having different numbers of repeat units. In general, the polyester compounds of Formula (I) have a number average molecular weight ($M_n$) of about 100 g/mol to about 200,000 g/mol. In some embodiments, the number average molecular weight of compounds of Formula (I) may range from about 100 g/mol to about 300 g/mol, from about 300 g/mol to about 1000 g/mol, from about 1000 g/mol to about 3000 g/mol, from about 3000 g/mol to about 10,000 g/mol, from about 10,000 g/mol to about 30,000 g/mol, from about 30,000 g/mol to about 100,000 g/mol, or greater than about 100,000 g/mol. In certain embodiments, the number average molecular weight of the compounds of Formula (I) may range from about 150 g/mol to about 5000 g/mol, from about 300 g/mol to about 4000 g/mol, from about 600 g/mol to about 3000 g/mol, or from about 800 g/mol to about 2000 g/mol.

In general, the polyester compounds disclosed herein are substantially biodegradable and compostable (per ASTM D6400), have low volatility, low toxicity, and/or can be used as flame retardants. As detailed below, the polyester compounds disclosed herein may be used as plasticizers to increase the flexibility and durability of polymers.

(II) Polymer Blend Compositions (a) Components

Another aspect of the present disclosure encompasses polymer blend compositions comprising polymers and polyester compounds of Formula (I). The polyester compounds are defined above in section (I). The polyester compounds of Formula (I) function as modifiers to improve one or more performance properties of polymers, such as, for example, increasing the flexibility and/or durability.

The identity of the polymer in the polymer composition can and will vary. In general, the polymer may be a thermoplastic polymer. In various embodiments, the polymer may be polyvinyl chloride, polylactide, poly(acrylic acid), poly(methacrylic acid), poly(methyl acrylate), poly(methyl methacrylate), poly(vinyl acetate), poly(vinyl alcohol), polyethylene, polystyrene, polypropylene, polycaprolactone, polyhydroxyalkanoate, polyurethane, cellulosics, polyacetal, polyamide, polyamine-imide, polyacrylonitrile, polybutadiene, polybutylene, polycarbonate, polydicyclopentadiene, polyketone, polyester, polyetheretherketone, polyetherimide, polyetheylenchlorinate, polyimide, polymethylpentene, polyethylene oxide, polyphenylene oxide, polyphenylene sulfide, polyphthalamide, polysulfone, silicone, copolymers thereof (e.g., acrylonitrile-butadiene-styrene, vinyl chloride-vinyl acetate, vinyl chloride-acrylate, vinyl chloride-methacrylate, etc.), or combinations of any of the aforementioned polymers. In specific embodiments, the polymer may be polyvinyl chloride (PVC) or polylactide (PLA).

The amount of the polyester compounds of Formula (I) included in the polymer blend compositions can and will vary. In some embodiments, the amount of the polyester compounds having Formula (I) included in the polymer blend composition may range from about 1 to about 100 parts by weight per hundred parts by weight of the polymer or resin (pphr). In various embodiments, the amount of the polyester compounds having Formula (I) present in the polymer blend composition may range from about 1 to about 3 pphr, from about 3 to about 10 pphr, from about 10 to about 30 pphr, or from about 30 to about 100 pphr. In other embodiments, the amount of the polyester compounds of Formula (I) included in the polymer blend composition may range from about 1 wt % to about 70 wt % by weight of the polymer blend composition. In certain embodiments, the amount of the polyester compounds of Formula (I) included in the polymer blend composition may range from about 1 wt % to about 3 wt %, from about 3 wt % to about 10 wt %, from about 10 wt % to about 30 wt %, or from about 30 wt % to about 70 wt % by weight of the polymer blend composition.

In embodiments in which the polymer blend composition comprises PVC, the amount of the polyester compounds of Formula (I) included in the PVC blend composition may range from about 5 to about 100 pphr. In various embodiments, the amount of the polyester compounds having Formula (I) included in the PVC blend composition may range from about 5 to about 10 pphr, from about 10 to about 20 pphr, from about 20 to about 30 pphr, from about 30 to about 40 pphr, from about 40 to about 50 pphr, from about 50 to about 60 pphr, from about 60 to about 70 pphr, from about 70 to about 80 pphr, from about 80 to about 90 pphr, or from about 90 to about 100 pphr.

In embodiments in which the polymer blend composition comprises PLA, the amount of the polyester compounds having Formula (I) included in the PLA blend composition may range from about 5 wt % to about 50 wt % by weight of the PLA blend polymer composition. In certain embodiments, the amount of the polyester compounds of Formula (I) present in the PLA blend composition may range from about 5 wt % to about 10 wt %, from about 10 wt % to about 15 wt %, from about 15 wt % to about 20 wt %, from about 20 wt % to about 25 wt %, from about 25 wt % to about 30 wt %, from about 30 wt % to about 40 wt %, or from about 40 wt % to about 50 wt % by weight of the PLA blend polymer composition.

(b) Properties of the Polymer Blend Compositions

The polymer blend compositions disclosed herein generally have lower glass transition temperatures ($T_g$) than those of unblended (or pristine) polymers. That is, the addition of polyester compounds of Formula (I) to a polymer reduces the $T_g$ of the polymer, thereby improving the flexibility and/or impact properties of the polymer. In general, the reduction in $T_g$ of the polymer blend compositions disclosed herein is correlated with the amount of the polyester compounds of Formula (I) incorporated into the polymer blend composition. For example, the $T_g$ of a polymer blend composition can be reduced to below room temperature simply by adding a sufficient amount of polyester compounds of Formula (I). The $T_g$ of the polymer blend compositions disclosed herein may be reduced by about 5° C. to about 10° C., by about 10° C. to about 20° C., by about 20° C. to about 30° C., by about 30° C. to about 40° C., by about 40° C. to about 50° C., by about 50° C. to about 60° C., or more than 60° C. relative to the $T_g$ of unblended polymers.

Additionally, the polymer blend compositions comprising PLA disclosed herein may have reduced cold crystallization temperature ($T_{cc}$) as compared to the $T_{cc}$ of unblended (or original) polymers. In general, the PLA polymer blend compositions disclosed herein have a significant drop of $T_{cc}$, which suggests an efficient plasticization and potentially increased crystallization rate during processing of the PLA polymer blend compositions. Thus, end products comprising PLA polymer blend compositions disclosed herein may have reduced production cycle times, with the end products having good crystallinity. In some embodiments, the $T_{cc}$ of the PLA polymer blend composition may be reduced by about 5° C. to about 10° C., by about 10° C. to about 20° C., by about 20° C. to about 30° C., by about 30° C. to about 40° C., by about 40° C. to about 50° C., by about 50° C. to about 60° C., or more than about 60° C. as compared to the $T_{cc}$ of unblended polymers.

Furthermore, the polymer blend compositions disclosed herein may have increased elongation at break as compared to that of unblended polymers. Typically, the polymer blend compositions disclosed herein have at least a 1.1-fold increase in elongation at break as compared to that of unblended polymers. In various embodiments, the elongation at break of the polymer blend compositions disclosed herein may be increased from about 1.1 to about 3-fold, from about 3-fold to about 10-fold, from about 10-fold to about 30-fold, from about 30-fold to about 100-fold, from about 100-fold to about 300-fold, or more than about 300-fold as compared to the elongation at break of unblended polymers. The polymer blend compositions also may have various (elongation) percentages at break. In some embodiments, the percentage at break may be from about 1 to about 10%, from about 10 to about 30%, from about 30 to about 100%, from about 100 to about 300%, from about 300 to about 1000%, or more than about 1000%.

The polymer blend compositions disclosed also may have reduced tensile modulus as compared to that of unblended polymers. In general, the polymer blend compositions disclosed herein have at least a 1% reduction in tensile modulus as compared to that of unblended polymers. In various embodiments, the tensile modulus of the polymer blend compositions disclosed herein may be reduced from about 1 to about 10%, from about 10 to about 20%, from about 20 to 30%, from about 30 to about 40%, from about 40 to about 50%, from about 50 to about 60%, from about 60 to about 70, from about 70 to about 80%, or more than about 80% as compared to the tensile modulus of unblended polymers.

The polymer blend compositions disclosed also may have reduced tensile strength at break as compared to that of unblended polymers. In general, the polymer blend compositions disclosed herein have at least a 1% reduction in tensile strength at break as compared to that of unblended polymers. In various embodiments, the tensile strength at break of the polymer blend compositions disclosed herein may be reduced from about 1 to about 10%, from about 10 to about 20%, from about 20 to 30%, from about 30 to about 40%, from about 40 to about 50%, from about 50 to about 60%, from about 60 to about 70, from about 70 to about 80%, or more than about 80% as compared to the tensile strength at break of unblended polymers.

(c) Optional Additives

The polymer blend compositions detailed above may further comprise at least one additive. Non-limiting examples of suitable additives include heat stabilizers, UV/light stabilizers, flame retardants/smoke suppressors, antioxidants, biocides, processing aids, thermal modifiers, impact modifiers, blowing agents, fillers, lubricants/co-stabilizers, pigments, and nucleating agents.

In some embodiments, the polymer blend composition may further comprise a heat stabilizer. Heat stabilizers generally comprise metal compounds such as metal soaps, metal salts, and organometallic compounds. The major metals contained in heat stabilizers include calcium, tin, zinc, barium, and lead. Non-limiting examples of suitable heat stabilizers include calcium-zinc stabilizer, calcium-organic stabilizer, (e.g., calcium acetylacetonate, zinc acetylacetonate), calcium stearate, zinc stearate, methyl tin stabilizer, organotin mercaptides, and combinations thereof.

In other embodiments, the polymer blend composition may further comprise a UV stabilizer or light stabilizer. Suitable UV stabilizers or light stabilizers include, without limit, 2-(2'-hydroxy-5'-methylphenyl)-benzotriazole, 2-hydroxy-4-octoxy benzophenone, 2-(2'-hydroxy-5'-tert-octylphenyl) benzotriazole, 2-(2'-hydroxy-3,5'-ditert-butylphenyl)-benzotriazole, 2-(2'-hydroxy-3,5'-ditert-butylphenyl)-5-chloro benzotriazole, 2-(2'-hydroxy-3'-tert-butyl-5'-methylphenyl)-5-chloro benzotriazole, 2-hydroxy-4-methoxy benzophenone, polyp-(2'-hydroxyethyl)-2,2,6,6-tetramethyl-4-hydroxy piperidylsuccinate, bis(2,2,6,6,-tetramethyl-4-piperidine) sebacate, 2-hydroxy-4-methoxy benzophenone-5-sulfonic acid, 2-phenyl-1H-benzo[d]imidazole-5-sulfonic acid, 2-(2'-hydroxy-3'-5'-ditert-butyl) benzotriazole, 2,2'-dihydroxy-4-methoxy benzotriazole, hindered amine light stabilizers (HALS), titanium dioxide and combinations thereof.

In still other embodiments, the polymer blend composition may further comprise a fire retardant or smoke suppressor. Non-limiting examples of suitable fire retardants/smoke suppressants include alumina trihydrate, magnesium hydroxide, antimony trioxide, hydromagnesite, copper clays, molybdates, borates, chlorendic acid derivatives, chlorinated paraffins, decabromodiphenyl ether, decabromodiphenyl ethane, brominated polystyrenes, brominated epoxy oligomers, tetrabromophthalic anhydride, tetrabisphenol A, hexabromocyclododecane, triphenyl phosphate, resorcinol bis(diphenylphosphate, bisphenol A diphenyl phosphate, tricresyl phosphate, dimethyl methyphosphonate, alumina diethyl phosphinate, tris(2,3-dibromopropyl phosphate, tris(1,3-dichloro-2-prpyl)phosphate, (2-chlorethyl)dichloroisopentyldiphosphate, and combinations thereof.

In further embodiments, the polymer blend composition may further comprise an antioxidant. Suitable antioxidants include without limit tetrakis[methylene(3,5-di-tert-butyl-4-hydroxyhydrocinnamate)]methane, octadecyl 3-(3,5-tertiary butyl-4-hydroxyl phenyl)propionate, tris-(2,4-tert-butylphenyl)phosphite, didodecyl 3,3-thiodipropinate, bis(2,4-dicumylphenyl)pentaerythritol diphosphite, hindered phenols, secondary aromatic amines, benzofuranones, and combinations thereof.

In other embodiments, the polymer blend composition may further comprise a biocide. Non-limiting examples of suitable biocide include copper 2-ethylhexanoate, zinc pyrithione, 10,10'-oxybisphenooxyarsine, diodomethyl-p-tolylsulfone, 3-iodo-2-propynyl butylcarbamate, N-(trichloromethylthio)phthalimide, n-octyl-, dichloro n-ocyl-isothiazolinone, butylbenzisothiazolinone, and combinations thereof.

In yet other embodiments, the polymer blend composition may further comprise a processing aid. Processing aids include, but are not limited to, acrylic processing aids, acrylate copolymers, styrene-acrylonitrile copolymers, methylmethacylate-styrene-vinylacetate copolymers, and combinations thereof.

In further embodiments, the polymer blend composition may further comprise a thermal modifier. Non-limiting examples of suitable thermal modifiers include methyacrylate-butadiene-styrene terpolymers (e.g., Clearstrength E-920), acrylonitrile-butadiene-styrene copolymers, alpha-methylstyrene copolymers, ethylene-propylene copolymers, ethylene copolymers, acrylate modifiers (e.g., phenoxyethyl methacrylate, ethylene glycol dimethacrylate, dimethacrylate, 1,3-butylene glycol, hexanediol dimethacrylate, trimethyacrylate ester, trimethyacrylate, trimethylolpropane), and combinations thereof.

In still other embodiments, the polymer blend composition may further comprise an impact modifier. Impact modifiers include without limit ethylene copolymers, ethylene/butyl acrylate/glycidyl methacrylate copolymers, ethylene-propylene copolymers, acrylic impact modifiers, acrylonitrile-butadiene-styrene copolymers, acrylonitrile-styrene-acrylate copolymers, styrene-butadiene-styrene copolymers, styrene-ethylene-butadiene-styrene copolymers, chlorinated polyethylene, crosslinked polyacrylate, and combinations thereof.

In alternate embodiments, the polymer blend composition may further comprise a blowing agent. Non-limiting examples of suitable blowing agents include azodicarbonamide or other azo-based compounds, hydrazine nitrate or other hydrazine-based compounds, endothermic chemical foaming agents (CFAs), exothermic CFAs, endothermic/exothermic CFA blends, hydrocarbons (e.g., pentane, isopentane, cyclopentane), isocyanate, and combinations thereof.

In other embodiments, the polymer blend composition may further comprise a lubricant or co-stabilizer. Suitable lubricants or co-stabilizers include without limit polyols, epoxidized esters, epoxidized oils, polyethylene waxes, oxidized polyethylene waxes, paraffins, metallic soaps (e.g., calcium stearate, zinc stearate, etc.), esters (e.g., polyethylene mono/di/tri stearate, glycerol monostearate, glyceryl monooleate, Montan wax, stearyl stearate, distearyl phthalate), amides (e.g., erucamide, oleamido, stearamide, ethylene bis(stearamide), and so forth), fatty acids (e.g., lauric acid, stearic acid, oleic acid, etc.), fatty alcohols (e.g., cetyl alcohol, stearyl alcohol, behenoyl alcohol, and so forth), and combinations thereof.

In further embodiments, the polymer blend composition may further comprise a filler. Non-limiting examples of suitable fillers include calcium carbonate, titanium dioxide, calcinated clay, glass, talc, mica, red mud, dolomite, and combinations thereof.

In still other embodiments, the polymer blend composition may further comprise a pigment. Suitable pigments include without limit titanium oxide, carbon black, jet black, red iron oxide, yellow iron oxide, benzimidazalone yellow, ultramarine violet, ultramarine blue, green pigment, orange pigment, and combinations thereof.

In embodiments in which the polymer blend composition comprises PLA, the composition may further comprise a nucleating agent. Non-limiting examples of suitable nucleating agents include N,N'-ethylene-bis-stearamide (EBS), LAK-301 (an aromatic sulfonate derivative), talc, sodium benzoate, calcium carbonate, calcium salts of suberic acid, calcium salts of pimelilc acid, beta-cyclodextrin, polyoxymethylene, magnesium, sodium, or zinc phenylphosphonate, cyanuric acid, uracil, thymine, nitroimidazole, and fatty acid amides.

The concentration of each optional additive in the polymer blend composition can and will vary. In general, the concentration of each additive may range from about 0.001 wt % to about 10 wt % of the polymer blend composition. In various embodiments, the concentration of each additive may range from about 0.001 wt % to about 0.01 wt %, from about 0.01 to about 0.1 wt %, from about 0.1 to about 1 wt %, or from about 1 to about 10 wt % of the polymer blend composition.

(d) Methods for Preparing Polymer Blend Compositions

The polymer blend compositions disclosed herein may be prepared using compounding methods that are well known to those skilled in the art. In some embodiments, the polymer blend compositions may be prepared by blending all the ingredients using a high-speed mixer or a ribbon blender. In other embodiments, the polymer blend compositions may be prepared by blending all the ingredients and then transferring the blend to a compounding extruder to produce a melt extrusion, which then can be cut into granules or pellets. The resultant polymer blend composition may be a powder, a granular material, or a pelletized material.

(III) Processes for Modifying Polymer Properties

Another aspect of the disclosure provides processes for improving performance properties of polymers. The processes comprise contacting polymers with polyester compounds of Formula (I) to form polymer blend compositions, wherein the polymer blend compositions have improved performance properties as compared to unblended polymers.

In some embodiments, the polymer blend composition has increased flexibility as compared to unblended (or unmodified) polymers. In other embodiments, the polymer blend composition has a reduced glass transition temperature as compared to unmodified polymer. In further embodiments, the polymer blend composition has a reduced cold crystallization temperature as compared to the unmodified polymer. In still other embodiments, the polymer blend composition has an increased elongation at break as compared to the unmodified polymer. In additional embodiments, the polymer blend composition has decreased tensile strength as compared to the unmodified polymer. In yet other embodiments, the polymer blend composition has decreased tensile strength at break as compared to the unmodified polymer. In alternate embodiments, the polymer blend composition has reduced hardness as compared to the unmodified polymer. In still other embodiments, the polymer blend composition has increased tear strength as compared to the unmodified polymer. In embodiments in which the polymer blend composition comprises PLA, the polymer blend composition has a reduced cycle time for production of end products comprising PLA.

Polyester compounds having Formula (I) are detailed above in section (I); suitable polymers are described above in section (II)(a), the ratio of the polyester compounds to the polymer is detailed above in section (II)(a), means for contacting the polymer with the polyester compounds are described above in section (II)(d).

(IV) Processes for Preparing Polyesters

Still another aspect of the present disclosure encompasses processes for preparing polyester compounds of Formula (I). Persons skilled in the art understand that a variety of different processes may be used to prepare the polyester compounds disclosed herein. Several processes are described below. In general, the processes comprise two steps. Step A entails an esterification/polymerization reaction that may be mediated by condensation or ring opening polymerization. Step B comprises an esterification or an alkylation reaction, thereby forming the hydrocarbyl terminated polyester compounds disclosed herein.

(a) Step A—Condensation

In some embodiments, the esterification/polymerization step is performed by condensation. Thus, step A comprises contacting a compound of Formula (III) with an alcohol, $R^3OH$, to form a distribution of compounds of Formula (II) in which k varies. The reaction is diagrammed below:

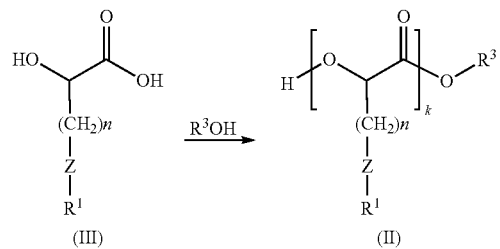

wherein $R^1$, $R^3$, Z, k, and n are as defined above in section (I).

The condensation reaction comprises contacting the compound of Formula (III) with an alcohol ($R^3OH$). The amount of alcohol that is contacted with the compound having Formula (III) can and will vary. In general, the mole-to-mole ratio of the compound having Formula (III) to $R^3OH$ may range from about 1:0.1 to about 1:10. In various embodiments, the mole-to-mole ratio of the compound having Formula (III) to $R^3OH$ may range from about 1:0.2 to about 1:8, from about 1:0.4 to about 1:6, from about 1:0.6 to about 1:5, from about 1:0.8 to about 1:4, from about 1:0.9 to about 1:3, or from about 1:1 to about 1:2.

In general, contact between the compound of Formula (III) and the alcohol is conducted in the presence of a catalyst. The catalyst may be a chemical catalyst, such as a proton donor, an organometallic compound, such as tin compounds, or another chemical catalyst known in the art. Alternatively, the catalyst may be an enzyme catalyst, such as a lipase enzyme. Lipase enzymes can catalyze the formation (as well as hydrolysis) of ester linkages.

In embodiments in which the catalyst is a proton donor, a variety of proton donors may be used in the process. Non-limiting examples of suitable proton donor include acid salts (e.g., bisulfates, hydrosulfates), mineral acids (e.g., hydrogen halides such as hydrochloric acid, hydrobromic acid; halogen oxoacids such as hypochloric acid, chloric acid, perchloric acid, periodic acid; sulfuric acid; boric acid; nitric acid, phosphoric acid, etc.); sulfonic acids (e.g., methanesulfonic acid, p-toluenesulfonic acid); solid bound proton donors (e.g., Amberlyst 15, Amberlyst 35, and the like); ion exchange resins (e.g., Amberlite, Amberjet, Dowex, etc.); ionomers (e.g., polystyrene sulfonate, Nafion, Hycar and so forth); and ionic liquids having acidic characteristics.

The mole-to-mole ratio of the compound of Formula (III) to the proton donor catalyst can and will vary depending upon the identity of the proton donor. In general, the mole-to-mole ratio of the compound having Formula (III) to the proton donor may range from about 1:0.005 to about 1:0.25. In some embodiments, the mole-to-mole ratio of the compound of Formula (III) to the proton donor may be about 1:0.01, about 1:0.02, about 1:0.04, about 1:0.05, about 1:0.06, about 1:0.08, about 1:0.10, about 1:0.12, about 1:0.14, about 1:0.16, about 1:0.18, or about 1:0.20.

The reaction may be conducted in the absence of a solvent or in the presence of a solvent. In embodiments in which a solvent is present, the type of solvent may vary depending upon the reactants. Thus, the solvent may be a nonpolar solvent, a polar solvent, or a combination thereof. Non-limiting examples of suitable nonpolar solvents include benzene, butyl acetate, tert-butyl methyl ether, chlorobenzene, chloroform, chloromethane, cyclohexane, dichloromethane (DCM), dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. Non-limiting examples of suitable polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In specific embodiments, the solvent may be toluene.

The volume-to-mass ratio of the solvent to the compound of Formula (III) can and will vary. Typically, the volume-to-mass ratio of the solvent to the compound of Formula (III) may range from about 1:1 to about 100:1. In various embodiments, the volume-to-mass ratio of the solvent to the compound of Formula (III) may range from about 1:1 to about 3:1, from about 3:1 to about 10:1, from about 10:1 to about 30:1, or from about 30:1 to about 100:1.

The reaction may be conducted at a temperature that ranges from about 30° C. to about 200° C. In certain embodiments, the temperature of the reaction may be about 40° C., 50° C., 60° C., 70° C., 80° C., 90° C., 100° C., 110° C., 120° C., 130° C., 140° C., or 150° C. In specific embodiments, the reaction may be conducted at a temperature from about 80° C. to about 150° C.

The duration of the reaction can and will vary. In general, the reaction may be allowed to proceed from about 1 hour to about 24 hours or more. In some embodiments, the reaction may be allowed to proceed overnight (or from about 12 to about 18 hours). Typically, however, the reaction is allowed to proceed for a sufficient period of time until the reaction has proceeded to the desired degree of completion, as determined by means well known to those of skill in the art. In embodiments in which the reaction is allowed to go to completion, a "completed reaction" generally means that the final reaction mixture contains a significantly diminished amount of the compound comprising Formula (III) and a significantly increased amount of the ester compound comprising Formula (II) compared to the amounts of each present at the beginning of the reaction.

The compounds of Formula (II) may be isolated from the reaction mixture by means known in the art. Suitable means include extracting, washing, precipitating, filtering, distilling, evaporating, drying, chromatography, and combinations thereof.

The yield of the compounds of Formula (II) can and will vary. In general, yield of the compounds will be at least about 20%, at least about 30%, at least about 40%, at least about 50%, at least about 60%, at least about 70%, at least about 80%, or at least about 90%.

(b) Step A—Ring Opening Polymerization

In other embodiments, the esterification and polymerization step is performed by a ring opening polymerization reaction. For this, a compound having Formula (IV) is contacted with an alcohol, $R^3OH$, to form a distribution of compounds having Formula (II) in which k varies. The reaction is diagrammed below:

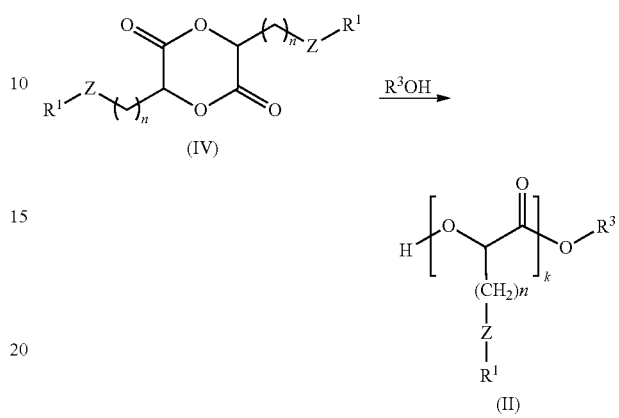

wherein $R^1$, $R^3$, Z, k, and n are as defined above in section (I).

The ring opening polymerization reaction comprises contacting the cyclic compound having Formula (IV) with an alcohol ($R^3OH$). In general, the mole-to-mole ratio of the compound of Formula (IV) to $R^3OH$ may range from about 1:0.1 to about 1:2. In various embodiments, the mole-to-mole ratio of the compound of Formula (IV) to $R^3OH$ may range from about 1:0.2 to about 1:1, from about 1:0.3 to about 1:0.9, from about 1:0.4 to about 1:0.8, or from about 1:0.5 to about 1:0.7.

In general, contact between the compound having Formula (IV) and the alcohol is conducted in the presence of a catalyst. Suitable catalysts and amounts to be included in the reaction mixture are detailed above in section (IV)(a). The reaction may be conducted in the absence or presence of a solvent, examples of which are detailed above in section (IV)(a). Suitable reaction temperatures, reaction times, optional isolation methods, and yields are described above in section (IV)(a).

(c) Step B—Esterification

In some embodiments, Step B comprises an esterification reaction. For this, the distribution of compounds of Formula (II) is contacted with an acyl halide or its acid analog, $R^4C(O)X$, to form a distribution of compounds of Formula (Ia), as shown below:

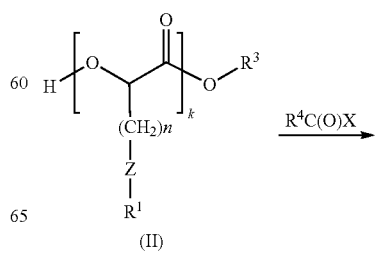

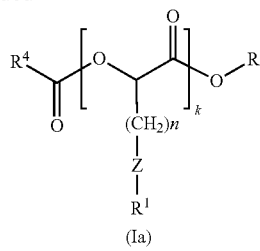

(Ia)

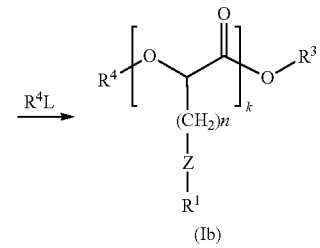

(II)     (Ib)

wherein $R^1$, $R^3$, Z, n, and k, are as defined above in section (I); $R^4$ is hydrocarbyl or substituted hydrocarbyl; and X is a halide ion or a hydroxyl group. When X is a hydroxyl group, $R^4C(O)X$ may be a fatty acid or a carboxylic acid. In specific embodiments, X may be chloride or bromide.

The amount of $R^4C(O)X$ that is contacted with the compounds of having Formula (II) can and will vary. In general, the mole-to-mole ratio of the compounds of Formula (II) to $R^4C(O)X$ may range from about 1:0.8 to about 1:1.5. In various embodiments, the mole-to-mole ratio of the compounds of Formula (II) to the $R^4C(O)X$ may range from about 1:0.9 to about 1:1.4, from about 1:1.0 to about 1:1.3, or from about 1:1.1 to about 1:1.2.

The reaction may be conducted in the absence of a solvent or in the presence of a solvent. In embodiments in which a solvent is present, suitable solvents are listed above in section (IV)(a).

The reaction may be conducted at a temperature that ranges from about 30° C. to about 200° C. In certain embodiments, the temperature of the reaction may be about 40° C., 50° C., 60° C., 70° C., 80° C., 90° C., 100° C., 110° C., 120° C., 130° C., 140° C., or 150° C. In specific embodiments, the reaction may be conducted at a temperature from about 70° C. to about 90° C. In general, the reaction will be conducted at atmospheric pressure.

The duration of the reaction can and will vary. In general, the reaction may be allowed to proceed from about 1 hour to about 24 hours or more. In some embodiments, the reaction may be allowed to proceed overnight (or from about 12 to about 18 hours). Typically, however, the reaction is allowed to proceed until the compound having Formula (II) is no longer detectable.

The compounds comprising Formula (Ia) may be isolated from the reactants in the reaction mixture by means known in the art. Suitable means include extracting, washing, precipitating, filtering, distilling, evaporating, drying, chromatography, and combinations thereof.

The yield of the compounds comprising Formula (Ia) can and will vary. In general, yield of the compound will be at least about 20%, at least about 30%, at least about 40%, at least about 50%, at least about 60%, at least about 70%, at least about 80%, or at least about 90%.

(d) Step B—Alkylation

In alternate embodiments, Step B comprises an alkylation reaction. For this, the compound(s) having Formula (II) is contacted with an alkylating agent, $R^4L$, to form a compound(s) having Formula (Ib), as shown below wherein $R^1$, $R^3$, Z, n, and k are as defined above in section (I); $R^4$ is hydrocarbyl or substituted hydrocarbyl; and L is a leaving group. Suitable leaving groups include halide ions (such as chloride, bromide, etc.) and sulfonate esters (such as tosylate, mesylate, and the like).

The amount of the alkylating agent ($R^4L$) that is contacted with the compounds of Formula (II) can and will vary. In general, the mole-to-mole ratio of the compounds having Formula (II) to the alkylating agent may range from about 1:0.1 to about 1:10. In various embodiments, the mole-to-mole ratio of the compounds having Formula (II) to the alkylating agent ($R^4L$) may range from about 1:01 to about 1:0.3, from about 1:0.3 to about 1:1, from about 1:1 to about 1:3, or from about 1:3 to about 1:10.

The reaction may be conducted in the absence of a solvent or in the presence of a solvent. In embodiments in which a solvent is present, suitable solvents are listed above in section (IV)(a). Suitable reaction temperatures, reaction times, optional isolation methods, and yields are described above in section (IV)(c).

(e) Optional Oxidation Reaction

In embodiments in which Z is sulfur in any of the compounds disclosed above, the compound(s) may undergo one or more oxidation reactions to convert Z into a sulfoxide or a sulfone.

A variety of oxidizing agents may be used in this process. Non-limiting examples of suitable oxidizing agents include peroxy acids (e.g., chloroperoxybenzoic acid, peracetic acid, peroxysulfuric acid), hydrogen peroxide, perchlorates, chlorite, hypochlorite, chlorate, sulfuric acid, persulfuric acid, hexavalent chromium compounds, permanganate compounds, sodium perborate, nitric acids, nitrate compounds, metal oxidants (such as, e.g., benezeneselenic acid, lead tetraacetate, osmium tetroxide, phosphomolybdic acid hydrate, pyridinium chlorochromate, pyridinium dichromate, quinolinium dichromate, and the like), and combinations thereof. In preferred embodiment, the oxidizing agent may be m-chloroperoxybenzoic acid or hydrogen peroxide.

The mole-to-mole ratio of the compound(s) of Formula (I), (Ia), (Ib) (II), (III), or (IV) to the oxidizing agent can and will vary. In general, the mole-to-mole ratio of the compound to the oxidizing agent may range from about 1:0.1 to about 1:20, from about 1:0.2 to about 1:10, from about 1:0.5 to about 1:5, or from about 1:1 to about 1:3.

The oxidation reaction may be performed in the presence of a solvent. The solvent may be a nonpolar solvent, a protic solvent, or an aprotic solvent depending upon the nature of the reactants. Suitable solvents are detailed above. The volume-to-mass ratio of the solvent to the compound of Formula (I), (Ia), (Ib) (II), (III), or (IV) can and will vary. Typically, the volume-to-mass ratio of the solvent to the compound may range from about 1:1 to about 60:1. In various embodiments, the volume-to-mass ratio of the solvent to the compound may range from about 4:1 to about 40:1.

The oxidation reaction may be conducted at a temperature that ranges from about −10° C. to about 50° C. In certain embodiments, the temperature of the reaction maybe about 0° C., about 10° C., about 20° C., about 25° C., or about 30° C. In one embodiment, the reaction may be allowed to proceed at about 0° C. In another embodiment, the reaction may be allowed to proceed for a first period of time at 0° C. and a second period of time at room temperature. In still another embodiment, the reaction may be conducted at room temperature. Typically, the reaction will be conducted at atmospheric pressure.

The duration of the reaction can and will vary. In general, the reaction may be allowed to proceed from several hours to several days. Typically, however, the reaction may be allowed to proceed for a sufficient period of time until the reaction is complete or substantially complete, as determined by means well known to those of skill in the art.

The compositions prepared according to the disclosures above can be optionally treated with one or more agents to remove color bodies and/or odor. Persons skilled in the art understand that a variety of different agents may be used to remove color bodies and/or odor from the compositions disclosed herein. In specific embodiments, the agent is charcoal.

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The terms "elongation" or "tensile elongation," as used herein, refer to a mechanical property of a polymer to deform or change shape when under tensile stress. When a polymer sample deforms by stretching, it becomes longer. Elongation is the percentage increase in original length. Elongation at yield refers to the point at which an increase in strain does not result in an increase in stress. "Elongation at break" corresponds to the point of rupture.

The "glass transition temperature" is the temperature at which a polymer transitions from a hard, glassy material to a soft, rubbery material.

The "cold crystallization temperature" is the temperature at which a polymer crystallizes.

As used herein, the term "pristine polymer" refers to a polymer that is devoid of additives.

The terms "tensile modulus" or "Young's modulus" refer to the stiffness of a material, and are used to describe the elastic properties of the material. Tensile modulus is defined as the ratio of stress (force per unit area) along an axis to strain (ratio of deformation over initial length) along that axis.

The term "tensile strength at break" refers to the tensile stress at the moment at which a test sample breaks. Tensile strength is the force placed on the test sample divided by the cross-sectional area of the sample.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes saturated hydrocarbyl groups that contain from 1 to 30 carbon atoms. They may be linear, branched, or cyclic, may be substituted as defined below, and include methyl, ethyl, propyl, isopropyl, butyl, hexyl, heptyl, octyl, nonyl, and the like.

The term "alkenyl" as used herein describes hydrocarbyl groups which contain at least one carbon-carbon double bond and contain from 1 to 30 carbon atoms. They may be linear, branched, or cyclic, may be substituted as defined below, and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes hydrocarbyl groups which contain at least one carbon-carbon triple bond and contain from 1 to 30 carbon atoms. They may be linear or branched, may be substituted as defined below, and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The term "aryl" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. They may be straight, branched, or cyclic. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

The following examples illustrate various embodiments of the invention.

Example 1: Polyester Composition with End Ethylhexyl Groups Prepared by Condensation Step A.
To 2-hydroxy-4-(methylthio)butanoic acid (88%, 60.4 g, 354 mmol) was added 2-ethyl-1-hexanol (41.5 g, 319 mmol), and Amberlyst 15 (6.10 g). The resulting mixture was heated under vacuum (53 mbar) with removal of water by raising the jacket temperature to 90° C. over the course of 1 hour. The jacket temperature was held at 90° C. for 10.5 hrs and then the vacuum was released and the reaction was cooled to room temperature, diluted with ethyl acetate (200 mL), and filtered. The solution was then washed with 5% sodium bicarbonate (2×50 mL), brine (3×50 mL), dried over magnesium sulfate, filtered and evaporated to give a yellow oil (80.1 g, 90%).

Step B.
The mixture obtained above (67 g) and 2-ethylhexanoyl chloride (43 g) were mixed together. The mixture was slowly heated to 80° C. to control the gas evolution. The mixture was held at 80° C. until the octyl 2-hydroxy-4-(methylthio)butanoate was consumed. The mixture then was cooled to 25° C. and 1 M aqueous NaOH (100 mL) was added. The mixture was stirred until the excess 2-ethylhexanoyl chloride was quenched. Methyl tert-butyl ether (100 mL) was added and the phases were separated. The organic phase was washed with water (100 mL) followed by brine (100 mL). The organic phase was dried and the solvent was removed by distillation under reduced pressure at 50° C. using a rotary evaporator. An orange-colored, viscous liquid (93 g) was obtained, comprising a mixture of 98% of compounds of Formula (I) in which k ranged from 1 to 4.

Example 2: Polyester Compound with End Decyl Groups Prepared by Condensation

Step A.
To a 4 neck 1 L round bottom flask fitted with a reflux condenser, dean stark trap, thermocouple, and mechanical overhead stirrer was added 2-hydroxy-4-(methylthio)butanoic acid (125 g, 832.2 mmol), 1-decanol (238 mL, 1248 mmol), sodium hydrogen sulfate (1.998 g, 16.64 mmol), and toluene (625 mL). The reaction was heated to reflux with removal of water (16 mL) during the course of about 6 hours and the reaction was monitored by GC analysis. The reaction was cooled to room temperature overnight and the organic layer was washed with saturated $NaHCO_3$ (1×300 mL), deionized water (1×300 mL), and brine (2×300 mL), dried over sodium sulfate, filtered and evaporated to give an amber oil (395.5 g). The oil was purified by kugelrohr distillation at 110° C. and 0.1 Torr vacuum to give an oil (105.2 g, 44%) comprising the monomer. m/z 313 ($MNa^+$)

Step B.
To the monomer prepared above (decyl 2-hydroxy-4-(methylthio)butanoate; 20.0 g, 69.0 mmol) was added 1-decanoyl chloride (16.5 mL, 79.5 mmol) and the solution was slowly heated to 80° C. to control the gas evolution. The mixture was held at 80° C. until the decyl 2-hydroxy-4-(methylthio)butanoate was consumed. The mixture was cooled to 25° C. and 1 M aqueous NaOH (30 mL) was added. The mixture was stirred until the excess 2-ethylhexanoyl chloride was quenched. Methyl tert-butyl ether (50 mL) was added and the phases were separated. The organic phase was washed with water (30 mL) followed by brine (30 mL). The organic phase was dried and the solvent was removed by distillation under reduced pressure at 50° C. using a rotary evaporator to give a light yellow liquid (31.4 g, quantitative) (m/z 467 ($MNa^+$), which consisted of 97% of the compound having Formula (I) in which k=1.

Example 3: Polyester Composition with End Ethylhexyl Groups Prepared by Ring Opening Polymerization (ROP)

Step A.
3,6-Bis[2-(methylthio)ethyl]-1,4-dioxane-2,5-dione (50 g, 189 mmol) and 2-ethyl-1-hexanol (24.7 g, 189 mmol) were dissolved in toluene (200 mL). 3 Å molecular sieves (20 g) and Amberlyst-15 (5 g) were added and the mixture was heated at 60° C. for several hours. The resin was filtered off and the toluene was removed using a rotary evaporator.

Step B.
2-Ethylhexanoyl chloride (31.4 g, 193 mmol) was added to the product from Step 1, and the mixture was slowly heated to 80° C. to control the gas evolution. The mixture was held at 80° C. until the 2-ethylhexyl 2-((2-hydroxy-4-(methylthio)butanoyl)oxy)-4-(methylthio)butanoate was consumed. The mixture was cooled to 25° C. and 1 M aqueous NaOH (200 mL) was added. The mixture was stirred until the excess 2-ethylhexanoyl chloride was quenched. Methyl tert-butyl ether (200 mL) was added and the phases were separated. The organic phase was washed with water (100 mL) followed by brine (100 mL). The organic phase was dried and the solvent was removed by distillation under reduced pressure at 50° C. using a rotary evaporator. An orange-colored, viscous liquid (91 g) was obtained comprising 91% of compound of Formula (I) with k=2 and 9% of other oligomeric compounds of Formula (I).

Example 4: Polyester Composition (Mn=800) Prepared by ROP

A 500 ml flask thermostated at 70° C. was charged with melted 3,6-bis (2-methylthio)ethyl-1,4-dioxane-2,5 dione (120.2 g, 454 mmol) under $N_2$ and a stirring bar. The system was completely flushed with dry $N_2$ for 0.5 hours. Then 1-octanol (36.1 mL, 29.75 g, 228 mmol) was added into the reactor, followed by addition of 0.01 ml of stannous octoate catalyst. The temperature of the system was raised to and maintained at 140° C. for about 9 hours. Analysis of the product gave Mn=770 g/mol, PDI=1.17, and consisted to 100% of compound of Formula ($R^2$=H) with k from 1 to 12.

Example 5: Polyester Composition (Mn=600) Prepared by ROP

Into a 500 ml flask was charged with melted 3,6-bis (2-methylthio)ethyl-1,4-dioxane-2,5 dione (197.4 g, 746 mmol) under $N_2$ and a stirring bar. The system was completely flushed with dry $N_2$ for 0.5 hours. The flask was thermostated at 70° C. Then 1-octanol (79.5 mL, 65.5 g, 503 mmol) was added into the reactor, followed by addition of 0.016 ml of stannous octoate catalyst. The temperature of the system was raised to and maintained at 140° C. for about 3.5 hours. Analysis of the product gave Mn=590 g/mol, PDI=1.15, and consisted of 100% of compound of Formula (I) ($R^2$=H) with k from 1 to 10.

Example 6: Polyester Composition with End Octyl Groups Prepared by ROP

An aliquot (50.2 g) of the product from Example 5 was weighed into a 2-necked 250 mL round bottom flask. A stir bar was added and the flask was equipped with a temperature probe and an external scrubber for HCl off gassing. Octanoyl chloride (18.6 mL; 17.74 g; 109.1 mmol) was added to the flask and the reaction was slowly warmed to 80° C., while stirring, under $N_2$ purge, for 16-18 hours. The reaction was cooled to room temperature and treated with 50 mL of 1M NaOH, and stirred under $N_2$. After 3 hours, 100 mL of methyl t-butyl ether was added and the layers separated. The aqueous layer was extracted once with 50 mL of methyl t-butyl ether and the organic layers were combined, washed with brine, dried over magnesium sulfate, filtered and concentrated to a clear light colored oil. The oil was dried on high vacuum line for 16-18 hours to give 63.01 g of a clear light yellow colored oil consisting of 100% of compound of Formula (I) with k from 1 to 10.

Example 7: Preparation of PLA Blends

Polymer blend compositions comprising PLA and the product from Example 4, Example 5, dioctyl adipate (DOA), or acetyl tributyl citrate (ATBC), were respectively prepared. Table 1 lists the compositions of PLA blends 1-5.

TABLE 1

PLA Blends

| Blend | PLA | Wt % | Mass | Plasticizer | Wt % | Mass |
|---|---|---|---|---|---|---|
| 1 | Ingeo 4032D | 80 | 1.6274 g | Example 4 | 20 | 0.4066 g |
| 2 | Ingeo 4032D | 75 | 1.5668 g | Example 5 | 25 | 0.5124 g |
| 3 | Ingeo 4032D | 80 | 1.6379 g | DOA | 20 | 0.4044 g |
| 4 | Ingeo 4032D | 80 | 1.7248 g | ATBC | 20 | 0.4365 g |
| 5 | Ingeo 3251D | 80 | 1.6708 g | Example 4 | 20 | 0.414 g |

The blends were prepared by dissolving the PLA resin and plasticizer in about 15 ml of anhydrous dichloromethane in a 40 ml vial. The solution was placed on a shaker to facilitate the dissolution over several days. Then the solution was poured on to a glass plate and solvent was evaporated. The film was thoroughly dried in a vacuum oven. Thermogravimetric analysis (TGA) showed less than 0.5% of residual solvent was detected.

Example 8: Evaluation of Plasticization and Acceleration of Crystallization of PLA Blends To evaluate the plasticization efficiency of the compounds disclosed herein, the glass transition temperature (Tg) and crystallization rate of PLA were evaluated by differential scanning calorimetry (DSC). Depression of $T_g$ is an indication of plasticization to show the increased polymer chain mobility. Crystallinity is a critical property in the application of PLA. In injection molding, the time it takes for pure PLA to develop a certain level of crystallinity in order to have high enough modulus and heat resistance for practical use is too long. Plasticizers/accelerants accelerate the crystallization rate of PLA by lowering the cold crystallization temperature ($T_{cc}$). Table 2 presents $T_g$, $T_{cc}$, and $T_m$ of pure PLA and the PLA blends prepared in Example 7.

TABLE 2

Plasticization and Acceleration of Crystallization of PLA

| | PLA 3251D | PLA 4032D | PLA Blend 1 | PLA Blend 2 | PLA Blend 3 | PLA Blend 4 | PLA Blend 5 |
|---|---|---|---|---|---|---|---|
| $T_g$ (° C.) | 57.6 | 56.4 | 29.8 | 22.2 | 42.5 | 20.6 | 31.1 |
| $T_{cc}$ (° C.) | 105.1 | 136.7 | 69.6 | 58.5 | 87.8 | 80.5 | 72.4 |
| $T_m$ (° C.) | 168.9 | 166.2 | 162.7 | 161.1 | 162 | 160.5 | 163 |

The data show that the compounds disclosed herein (i.e., Blends 1, 2, and 5) efficiently plasticized PLA by significantly decreasing $T_g$ of PLA. The decrease in $T_g$ is comparable to the that of traditional plasticizers such as DOA and ATBC. Furthermore, $T_{cc}$ of the blends comprising the compounds disclosed herein were as low as 69.6° C., much lower than that of the traditional accelerants DOA and ATBC, when included at the same inclusion rate of 20 wt %.

Example 9: Evaluation of the Mechanical Properties of PLA Blends

Blends of PLA and plasticizers were prepared using a Brabender mixer and the mixture was compression molded into films of 0.26 mm at 190° C. PLA blend 6 contained 85 wt % PLA (Ingeo 4060D) and 15 wt % of 3,6-bis (2-methylthio)ethyl-1,4-dioxane-2,5 dione. PLA blend 7 contained 80 wt % PLA (4032D) and 20 wt % of the product from Example 4.

The molded films were tested with dynamic-mechanical thermal analysis (DTMA) and tensile tester for mechanical properties per ASTM D882. As controls, pure PLA was processed under the same compounding and molding conditions described above. Table 3 presents the data.

TABLE 3

Mechanical properties of PLA

| Sample | $T_g$ (° C.) | $T_{cc}$ (° C.) | Tensile Strength at Yield (MPa) | Elongation at Yield (%) | Elongation at Break (%) | Modulus (KPSI) |
|---|---|---|---|---|---|---|
| PLA alone (Ingeo 4060D) | 63 | — | 27.6 | 4.6 | 6.0 | 124.8 |
| PLA Blend 6 | 40.0 | — | 18.6 | 4.1 | 44.2 | 121 |
| PLA alone (Ingeo 4032D) | 67.5 | 120 | 42.5 | 4.3 | 5.3 | 133.5 |
| PLA Blend 7 | 20.8 | 80.4 | 33.2 | 5.9 | 288.6 | 81.4 |

The plasticizers disclosed herein increased plasticity (i.e., lowered $T_g$ and $T_{cc}$) and increased elongation at break, while maintaining good tensile strength and modulus. The increase in flexibility was significant; e.g., PLA blend 7 increased elongation at break by more than 50-fold and PLA blend 6 increased elongation at break by about 7-fold.

Example 10: Evaluation of the Mechanical Properties of PVC Blends

Polymer blend compositions comprising PVC and the product of Examples 5, Example 3, or diisononyl phthalate (DINP) were prepared. The plasticizers were evaluated at two inclusion rates (i.e., 20 or 50 parts per hundred parts of resin (pphr)). Each blend also contained antimony trioxide (3 parts), calcium zinc stabilizer (8 parts), sterically hindered phenolic antioxidant (Irganox 1010) (1 part), and epoxide soybean oil (3 parts). Table 4 lists the compositions of the PVC blends.

TABLE 4

PVC Blends

| Blend | Plasticizer | Plasticizer (pphr) | PVC (parts) |
|---|---|---|---|
| 1 | DINP | 20 | 100 |
| 2 | DINP | 50 | 100 |
| 3 | Example 5 | 20 | 100 |
| 4 | Example 5 | 50 | 100 |
| 5 | Example 3 | 20 | 100 |
| 6 | Example 3 | 50 | 100 |
| 7 | Example 1 | 50 | 100 |
| 8 | Example 2 | 50 | 100 |
| 9 | Example 6 | 50 | 100 |

The mechanical properties of the PVC blends were tested per ASTM D882. Table 5 presents the results.

TABLE 5

Mechanical properties of PVC Blends

| Material | Tensile Strength (KPSI) at Break | Tensile Strength (KPSI) at 100% Elongation | Elongation at Break (%) | Modulus (KPSI) |
|---|---|---|---|---|
| PVC Blend 1 | 1.88 | — | 60.9 | 17.1 |
| PVC Blend 2 | 1.67 | 1.25 | 281.2 | 1.74 |
| PVC Blend 3 | 3.29 | — | 207.6 | 46.2 |
| PVC Blend 4 | 2.09 | 1.38 | 340.6 | 1.75 |
| PVC Blend 5 | 3.34 | — | 245.4 | 46.2 |
| PVC Blend 6 | 1.98 | 0.63 | 347.5 | 2.98 |
| PVC Blend 7 | 1.60 | — | 318.8 | 1.08 |
| PVC Blend 8 | 1.39 | — | 369.0 | 0.72 |
| PVC Blend 9 | 2.23 | — | 341.6 | 2.22 |

These data show that the plasticizers disclosed herein significantly improved flexibility of PVC for plasticization meanwhile maintaining a good tensile strength and modulus. These plasticizers outperform the industry standard DINP for tensile properties.

What is claimed is:

1. A composition comprising compounds of Formula (I):

$$R^2 + O \underset{(CH_2)_n}{\overset{O}{\underset{|}{\text{-}}}}\underset{|}{\overset{}{\text{-}}} \underset{k}{\overset{}{\text{-}}} O - R^3 \quad \text{(I)}$$

with $(CH_2)_n$—Z—$R^1$ branch wherein:
  $R^1$ and $R^3$ independently are hydrocarbyl or substituted hydrocarbyl;
  $R^2$ is $R^4(O)C-$, wherein $R^4$ is hydrocarbyl or substituted hydrocarbyl;
  Z is sulfur;
  k is an integer of 1 or greater; and
  n is an integer of 1 or greater.

2. The composition of claim 1, wherein $R^1$ is alkyl; and $R^3$ and $R^4$ independently are alkyl, substituted alky, alkenyl, or substituted alkenyl.

3. The composition of claim 1, wherein $R^1$ is $C_1$ to $C_6$ alkyl; and $R^3$ and $R^4$ independently are $C_1$ to $C_{30}$ alkyl or $C_1$ to $C_{30}$ alkenyl.

4. The composition of claim 1, wherein $R^1$ is methyl; k is from 1 to 20; and n is 2.

5. The composition of claim 1, wherein the composition is used as a plastic modifier.

6. A polymer blend composition comprising a polymer and a composition comprising compounds of Formula (I):

$$R^2 + O \underset{(CH_2)_n}{\overset{O}{\underset{|}{\text{-}}}}\underset{|}{\overset{}{\text{-}}} \underset{k}{\overset{}{\text{-}}} O - R^3 \quad \text{(I)}$$

with $(CH_2)_n$—Z—$R^1$ branch wherein:
R$^1$ and R$^3$ independently are hydrocarbyl or substituted hydrocarbyl;
R$^2$ is R$^4$(O)C—, wherein R$^4$ is hydrocarbyl or substituted hydrocarbyl;
Z is sulfur;
k is an integer of 1 or greater; and
n is an integer of 1 or greater.

7. The polymer blend composition of claim 6, wherein R$^1$ is alkyl; and R$^3$ and R$^4$ independently are alkyl, substituted alky, alkenyl, or substituted alkenyl.

8. The polymer blend composition of claim 6, wherein R$^1$ is C$_1$ to C$_6$ alkyl; and R$^3$ and R$^4$ independently are C$_1$ to C$_{30}$ alkyl or C$_1$ to C$_{30}$ alkenyl.

9. The polymer blend composition of claim 6, wherein herein R$^1$ is methyl; k is from 1 to 20; and n is 2.

10. The polymer blend composition of claim 6, wherein the polymer is chosen from polyvinyl chloride, polylactide, poly(acrylic acid), poly(methacrylic acid), poly(methyl acrylate), poly(methyl methacrylate), poly(vinyl acetate), poly(vinyl alcohol), polyethylene, polystyrene, polypropylene, polycaprolactone, polyhydroxyalkanoate, polyurethane, cellulosics, copolymer thereof, or combination thereof.

11. The polymer blend composition of claim 6, wherein the polymer composition has a reduced glass transition temperature, reduced cold crystallization temperature, increased elongation at break, improved tensile modulus, improved reduced tensile strength at break, or combination thereof, relative to that of an unblended polymer.

12. The polymer blend composition of claim 6, wherein the polymer is polyvinyl chloride and the composition comprising compounds of Formula (I) is present at a concentration from about 5 to about 100 parts by weight per hundred parts by weight of the polymer.

13. The polymer blend composition of claim 6, wherein the polymer is polylactide and the composition comprising compounds of Formula (I) is present at a concentration from about 5 wt % to about 50 wt % by weight of the polymer blend composition.

14. The polymer blend composition of claim 6, further comprising at least one additive chosen from a heat stabilizer, a UV/light stabilizer, a flame retardant/smoke suppressor, an antioxidant, a biocide, a processing aid, a thermal modifier, an impact modifier, a blowing agent, a filler, a lubricant/co-stabilizer, a pigment, or a nucleating agent.

15. The polymer blend composition of claim 6, wherein the polymer blend composition is a powder, a granular material, or a pelletized material.

16. A process for modifying performance properties of polymers, the process comprising contacting a polymer with a composition comprising compounds of Formula (I) to form a polymer blend composition, wherein the polymer blend composition has an improved performance property relative to an unmodified polymer, the compounds of Formula (I):

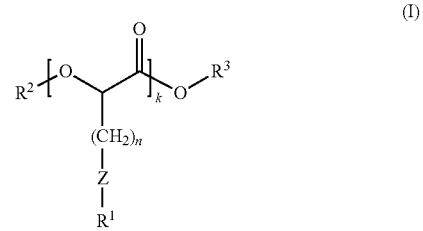

wherein:
R$^1$ and R$^3$ independently are hydrocarbyl or substituted hydrocarbyl;
R$^2$ is R$^4$(O)C—, wherein R$^4$ is hydrocarbyl or substituted hydrocarbyl;
Z is sulfur;
k is an integer of 1 or greater; and
n is an integer of 1 or greater.

17. The process of claim 16, wherein R$^1$ is alkyl; and R$^3$ and R$^4$ independently are alkyl, substituted alky, alkenyl, or substituted alkenyl.

18. The process of claim 16, wherein R$^1$ is C$_1$ to C$_6$ alkyl; and R$^3$ and R$^4$ independently are C$_1$ to C$_{30}$ alkyl or C$_1$ to C$_{30}$ alkenyl.

19. The process of claim 16, wherein R$^1$ is methyl; k is from 1 to 20; and n is 2.

20. The process of claim 16, wherein the polymer is chosen from polyvinyl chloride, polylactide, poly(acrylic acid), poly(methacrylic acid), poly(methyl acrylate), poly(methyl methacrylate), poly(vinyl acetate), poly(vinyl alcohol), polyethylene, polystyrene, polypropylene, polycaprolactone, polyhydroxyalkanoate, polyurethane, cellulosics, copolymer thereof, or combination thereof.

21. The process of claim 16, wherein the improved performance property is reduced glass transition temperature, reduced cold crystallization temperature, increased elongation at break, reduced tensile modulus, reduced tensile strength at break, or combination thereof.

22. The process of claim 16, wherein the polymer is polyvinyl chloride and the composition comprising compounds of Formula (I) is present at a concentration from about 5 to about 100 parts by weight per hundred parts by weight of the polymer.

23. The process of claim 16, wherein the polymer is polylactide and the composition comprising compounds of Formula (I) is present at a concentration from about 5 wt % to about 50 wt % by weight of the polymer blend composition.

* * * * *